(12) United States Patent
Kimura et al.

(10) Patent No.: US 8,507,252 B2
(45) Date of Patent: Aug. 13, 2013

(54) PLANT DISEASE CONTROLLING COMPOSITION, PLANT DISEASE CONTROLLING METHOD, AND NOVEL MICROORGANISM

(75) Inventors: Shinya Kimura, Toyonaka (JP); Masashi Fujinaga, Nagano (JP)

(73) Assignees: Sumitomo Chemical Company, Limited, Tokyo (JP); Nagano Prefecture, Nagano-Shi (JP)

( * ) Notice: Subject to any disclaimer, the term of this patent is extended or adjusted under 35 U.S.C. 154(b) by 0 days.

(21) Appl. No.: 13/140,450

(22) PCT Filed: Dec. 18, 2009

(86) PCT No.: PCT/JP2009/071171
§ 371 (c)(1),
(2), (4) Date: Jun. 17, 2011

(87) PCT Pub. No.: WO2010/071204
PCT Pub. Date: Jun. 24, 2010

(65) Prior Publication Data
US 2011/0256102 A1 Oct. 20, 2011

(30) Foreign Application Priority Data
Dec. 19, 2008 (JP) ................................. 2008-324483

(51) Int. Cl.
*C12N 1/00* (2006.01)
*A01N 63/00* (2006.01)

(52) U.S. Cl.
USPC ...................... 435/254.1; 424/93.5

(58) Field of Classification Search
USPC ...................... 424/93.5; 435/254.1
See application file for complete search history.

(56) References Cited

U.S. PATENT DOCUMENTS
2002/0177528 A1  11/2002  Zhang et al.

FOREIGN PATENT DOCUMENTS
JP  6-24924 A  2/1994

OTHER PUBLICATIONS

Cerkauskas "*Fusarium* Yellows of Celery" Ontario: Ministry of Agriculture, Food, and Rural Affairs, 2006 available at www.omafra.gov.on.ca/english/crops/facts/fusarium_celery.htm.*
Hujslova "Diversity of fungal communities in saline and acidic soils in the Soos National Natural Reserve, Czech Republic" Mycological Progress, 9 (1), 2010 1-15, sequence deposited Oct. 31, 2008.*
Chung et al., Potential of an Indigenous Fungus, *Plectosporium tabacinum*, as a Mycoherbicide for Control of Arrowhead (*Sagittaria trifolia*), Plant Disease, vol. 82, No. 6, Jun. 1998, pp. 657-660.
Hujslova et al., Accession No. FJ430714, Database DDBJ/EMBL/Genbank[online], uploaded Nov. 26, 2008, 7 pages.
International Preliminary Report on Patentability and English translation of the Written Opinion of the International Searching Authority for International Application No. PCT/JP2009/071171 dated Jul. 5, 2011 (Forms PCT/IB/373 and PCT/ISA/237).
International Search Report for International Application No. PCT/JP2009/071171 dated Mar. 9, 2010.
Jacobs et al., "Interactions between nematophagous fungi and consequences for their potential as biological agents for the control of potato cyst nematodes", Mycol. Res., vol. 107, Issue 1, Jan. 2003, pp. 47-56.
Pitt et al., "*Plectosporium* alismatis comb. nov. a new placement for the Alismataceae pathogen *Rhynchosporium* alismatis", Mycol. Res., vol. 108, Issue 7, Jul. 2004, pp. 775-780.
Zhang et al., "Evaluation of *Plectosporium tabacinum* for control of herbicide-resistant and herbicide-susceptible false cleavers", Weed Science, vol. 50, 2002, pp. 79-85.
The Requirements Stated by the Examiner for corresponding Mexican Patent Application No. MX/a/2011/006504, dated Jan. 31, 2013.
Supplementary European Search Report for corresponding European Patent Application No. 09833506.0, dated Mar. 26, 2013.

* cited by examiner

*Primary Examiner* — Blaine Lankford
*Assistant Examiner* — Charles Zoltan Constantine
(74) *Attorney, Agent, or Firm* — Birch, Stewart, Kolasch & Birch, LLP

(57) ABSTRACT

Disclosed are a plant disease controlling composition that contains as an active ingredient a microorganism belonging to genus *Plectosphaerella* and having a plant disease controlling ability; a plant disease controlling method that uses said composition; and a novel microorganism that belongs to genus *Plectosphaerella* and has a plant disease controlling ability.

6 Claims, No Drawings

PLANT DISEASE CONTROLLING COMPOSITION, PLANT DISEASE CONTROLLING METHOD, AND NOVEL MICROORGANISM

TECHNICAL FIELD

The present invention relates to a plant disease controlling composition, a plant disease controlling method, and a novel microorganism.

BACKGROUND ART

Heretofore, various methods for controlling soil-borne plant diseases are known, including soil disinfection, the use of resistant cultivars or resistant rootstocks, etc. Among them, soil fumigants exhibit a higher effect, but lead to problems with environmental conservation and worker's safety. Recently, specially cultivated agricultural products or organic agricultural products have received attention in view of food safety, and thus controlling methods alternative to the use of chemical pesticides have been studied. In these situations, agents for controlling diseases and pestilences (i.e., agents capable of controlling damages caused by phytopathogenic microorganisms or pests), which utilize microorganisms, have been researched and developed, including microorganism pesticides containing filamentous fungi or bacteria as an active ingredient.

Genus *Plectosphaerella* is a filamentous fungus widely distributed around the world, which has been studied as microorganism pesticides for controlling nematodes such as cyst nematode or weeds such as catchweed (see, for example, Non-Patent Literature 1 and Patent Literature 1). However, it has not reported that microorganisms belonging to genus *Plectosphaerella* have a controlling effect on plant diseases.

CITATION LIST

Patent Literature

Patent Literature 1: U.S. patent publication No. 2002/0177528

Non-Patent Literature

Non-Patent Literature 1: "Mycological Research" (GB), January 2003, Vol. 107, No. 1, p. 47-56

SUMMARY OF INVENTION

Technical Problem

The objects of the present invention are to provide a plant disease controlling composition having a controlling effect on plant diseases, a plant disease controlling method and a novel microorganism.

Solution to Problem

The present inventors have intensively studied to accomplish the above objects and finally found that filamentous fungi belonging to genus *Plectosphaerella* (anamorphic genus *Plectosporium*) have a plant disease controlling activity, thereby reaching the present invention.

That is, the present invention includes the following embodiments:

[1] A plant disease controlling composition comprising as an active ingredient a microorganism belonging to genus *Plectosphaerella* and having a plant disease controlling ability.
[2] The plant disease controlling composition according to the above [1], wherein the plant disease is a disease caused by genus *Fusarium*.
[3] The plant disease controlling composition according to the above [2], wherein the disease caused by genus *Fusarium* is celery yellows, lily rot, tomato wilt, or aster wilt.
[4] The plant disease controlling composition according to any of the above [1] to [3], wherein the microorganism is *Plectosphaerella* sp. strain KFC005 (FERM BP-11196), or *Plectosphaerella* sp. strain KFC015 (FERM BP-11197).
[5] A method for controlling a plant disease, which comprises applying an effective amount of the plant disease controlling composition according to any of the above [1] to [4] to a plant or an area in which a plant is grown.
[6] *Plectosphaerella* sp. strain KFC005 (FERN BP-11196).
[7] *Plectosphaerella* sp. strain KFC015 (FERN BP-11197).
[8] A method for producing a microorganism, which comprises culturing a microorganism belonging to genus *Plectosphaerella* and having a plant disease controlling ability in a solid medium or a liquid medium.

Effects of Invention

The plant disease controlling composition of the present invention exhibits a plant disease controlling effect.

DESCRIPTION OF EMBODIMENTS

The microorganism belonging to genus *Plectosphaerella* and having a plant disease controlling ability in the present invention (hereinafter also referred to as "the microorganism of the present invention") can be separated and selected by, for example, the following procedures.

1. A section is produced from a vascular tissue of root of a plant showing no disease symptoms (healthy plant) in an agricultural field where a plant disease such as *Fusarium* diseases occurs at a high level.
2. The section is placed onto the flat surface of a plain agar medium containing 50 ppm of chloramphenicol, and then the medium is put into an incubator at 25° C. and allowed to stand for culturing microorganisms present in the section.
3. The hyphal tips of microorganisms extending from the section are transplanted onto the flat surface of a plain agar medium to culture them.
4. The microorganisms obtained by the procedure described in the above 3 are transplanted onto the surface of a potato extract agar medium containing glucose, and then microorganisms having the conidium formed on the condiophore are collected.
5. The microorganisms collected by the procedure described in the above 4 are cultured on a PDA flat medium at 25° C. for 14 days. From the microorganisms obtained by the above culture, a microorganism showing the following features is separated.

Pale orange—cream colored, moist colonies with a flat surface are formed.

Condiophore rising perpendicularly from vegetative hypha is unbranched or branched.

Cylindrical two-cell conidia is mainly formed in the conidium mass at the tip of phialide (conidium-forming cells).

6. The microorganisms obtained by the procedure described in the above 5 are assessed for the controlling activity on plant diseases by a known method to select a microorganism having a plant disease controlling ability.

The plant disease in the assessment test of controlling activity is generally a disease occurred at a high level in an agricultural field, from where the microorganisms to be tested are separated. For example, microorganisms separated from a healthy plant showing no disease symptoms in an agricultural field where celery yellows occurs at a high level are assessed for the controlling activity on celery yellows.

In addition, the plant disease in the assessment test of controlling activity may be different from a disease occurred at a high level in an agricultural field, from where the microorganisms to be tested are separated. For example, microorganisms separated from a healthy plant showing no disease symptoms in an agricultural field where celery yellows occurs at a high level may be assessed for the controlling activity on aster wilt to select a microorganism having plant disease controlling ability.

In the present invention, the "plant disease controlling activity" refers to an activity showing not less than 40 of the controlling value represented by the following formula.

Controlling value=100×[1−(disease severity of treated section/disease severity of non-treated section)]

In the above formula, the treated section means a sample treated with a microorganism to be tested.

In the assessment test of the controlling activity, the amount of microorganisms to be treated is typically $10^3$ to $10^{15}$ CFU/plant (CFU: colony forming unit), preferably $10^3$ to $10^{12}$ CFU/plant, and more preferably $10^5$ to $10^{10}$ CFU/plant.

7. The BLAST homology search of the microorganisms selected by the procedure described in the above 6 is conducted for 28S-rDNA-D1/D2 base sequence by using international base sequence databases such as GenBank/DDBJ/EMBL to select a microorganism having a homology of not less than 95% to genus *Plectosphaerella*.

Examples of the microorganism of the present invention include *Plectosphaerella* sp. strain KFC005 (FERM BP-11196), and *Plectosphaerella* sp. strain KFC015 (FERM BP-11197).

The microorganism of the present invention can be produced in a large scale by culturing it in a liquid medium or a solid medium.

The culture medium, which is not particularly limited as long as the microorganism of the present invention can grow in the medium, generally contains a carbon source, a nitrogen source, etc. which are typically used in the culture of microorganisms.

The liquid medium can be generally prepared by appropriately mixing water with a carbon source, a nitrogen source, etc.

Examples of the carbon source include sugars such as glucose, dextrin and sucrose; sugar alcohols such as glycerol; organic acids such as fumaric acid, citric acid and pyruvic acid; animal or vegetable oils; and molasses.

Examples of the nitrogen source include natural organic nitrogen sources such as meat extract, peptone, yeast extract, malt extract, soybean powder, corn steep liquor, cotton seed powder, dried yeast and casamino acid; ammonium salts or nitrates of inorganic acids such as sodium nitrate, ammonium chloride, and ammonium phosphate; ammonium salts of organic acids such as ammonium fumarate, ammonium citrate; urea; and amino acids.

In the liquid medium, in addition to the above ammonium salts, other salts may be used. Examples of the salt include chlorides such as potassium chloride, sodium chloride, magnesium chloride, ferrous chloride, manganese chloride, cobalt chloride, zinc chloride; sulfates, acetates, carbonates, and phosphates, especially, sodium chloride, potassium chloride, magnesium sulfate, ferrous sulfate, manganese sulfate, cobalt chloride, zinc sulfate, copper sulfate, sodium acetate, calcium carbonate, sodium carbonate, potassium monohydrogen phosphate, and potassium dihydrogen phosphate.

Examples of the solid medium include those containing main cereals such as rice and wheat; coarse cereals such as, maize, millet, barnyard grass, kaoliang and buckwheat; or mixtures thereof; those containing as a main ingredient sawdust, bagasse, rice hulls, peas, straw, corn cob or cotton seed lees, and optionally rice bran, corn bran, corn steep liquor, yeast powder, wheat bran, amino acids, soy meal, flour, tofu refuse, glucose, maltose extract, mineral (monopotassium phosphate, carbonated coal, calcium sulfate, magnesium sulfate and the like) or vitamin (such as thiamin); those containing as a carrier a porous material such as clay minerals or naturally-occurring macromolecules such as agar and gelatin, and the carbon source, the nitrogen source, others such as salts, and the like.

The culture of the microorganism of the present invention can be carried out according to a common method which is generally used for the culture of microorganisms. Examples of the culture method using a liquid medium include tube shake culture, reciprocal culture, jar fermenter, and tank culture. Examples of the culture method using a solid medium include stationary culture.

The culture time may vary depending on the culture conditions, which is generally in the range of about 1 day to about 2 months.

The microorganism of the present invention can be collected, for example, by centrifuging the liquid culture medium after the culture of the microorganism of the present invention, or by adding a distillated water, etc. to the solid culture medium after the culture of the microorganism of the present invention and then taking a scraping of the microorganism bodies from the surface.

Next, the plant disease controlling composition of the present invention (hereinafter also referred to as "the composition of the present invention") will be explained below.

The composition of the present invention contains the microorganism of the present invention as an active ingredient.

In the composition of the present invention, the microorganism of the present invention is generally a viable microorganism body. The viable microorganism body includes conidium, mycelium and the like, which may be used alone or in combination.

In the composition of the present invention, the body of the microorganism of the present invention may be used itself, or generally formulated into solid formulations such as dusts, granules and wettable powders, or liquid formulations such as emulsifiable concentrates, suspension concentrates and oil solutions. These formulations may contain the body of the microorganism of the present invention, and a solid carrier or a liquid carrier, and if necessary, adjuvants for formulation such as surfactants, water retention agents, desiccants, and deoxidants.

These formulation typically contain $10^3$ to $10^{15}$ CFU (CFU: colony forming unit) of the microorganism of the present invention per g of the formulation.

Examples of the solid carrier include clays such as serite, kaolin clay, diatomaceous earth, synthetic hydrated silicon oxide, bentonite, Fubasami clay and acid clay; talcs; ceramics; other inorganic minerals; and organic materials such as peat moss, pulp, agar, bran, etc.

Examples of the liquid carrier include water, aliphatic hydrocarbons such as hexane, kerosene and light oil; horticultural oils such as machine oil; ester oils such as soy oil and cotton seed oil; and silicone oils.

Examples of the surfactant include anionic surfactants such as sulfuric ester salts, sulfonates, or phosphoric ester salts; cationic surfactants such as amine salts, or quaternary ammonium salts; ampholytic surfactants such as amino acid types, or betaine types; nonionic surfactants such as polyethylene glycol types, or polyhydric alcohol types. The surfactant may be used alone or in combination of two or more thereof.

Examples of the water retention agent include adhesive polysaccharides such as carrageenan, xanthane gum, sodium alginate, carboxyrmethylcellulose and sodium hydroxyethylcellulose; adhesive synthetic water soluble polymers such as sodium polyacrylate, polyethyleneimine, polyvinyl alcohol, polyethylene oxide and polyvinyl pyrolidone; adhesive animal polymers such as sodium chondroitin sulfate, casein and gelatin; polyhydric alcohols such as glycerin and ethyleneglycol; and the like. The water retention agent may be used alone or in combination of two or more thereof.

Examples of the desiccant include silicon oxide compounds such as silicon dioxide, silica gels, zeolite, and molecular sieves, calcium compounds such as calcium oxide, calcium chloride and calcium sulfate, clay, etc. The desiccant may be used alone or in combination of two or more thereof.

Examples of the deoxidant include ferrous deoxidants or organic deoxidants. The above deoxidant may be used alone or in combination of two or more thereof.

Examples of the pathogenic microorganisms of plant diseases on which the composition of the present invention has a controlling effect include the following microorganisms:
bacteria such as those causing bacterial wilt (genus *Pseudomonas*), bacterial soft rot (genus *Erwinia*), crown gall (genus *Agrobacterium*), damping-off (genus *Pseudomonas*), bacterial grain rot (genus *Pseudomonas*), brown stripe (genus *Pseudomonas*); actinomycetes such as those causing scab (genus *Streptomyces*);
filamentous fungi such as those causing clubroot (genus *Plasmodiophora*), Phytophthora rot (genus *Phytophthora*), Pythium snow blight (genus *Phthium*), Verticillium wilt (genus *Verticillium*), mealybug wilt (genus *Fusarium*), yellows (genus *Fusarium*), root rot (genus *Fusarium*), dry rot (genus *Fusarium*), black scurf (genus *Rhizoctonia*), violet root rot (genus *Helicobaasidium*), white root rot (genus *Rosellinia*), southern blight (genus *Corticium*), brown root rot (genus *Pyrenochaeta*), Cephalosporium stripe (genus *Cephalosporium*), dry rot (genus *Cylindrocarpon*), root necrosis (genus *Cylindrocladium*), snow mold (genus *Typhula*), Aphanomyces root rot (genus *Aphanomyces*), "Bakanae" disease (genus *Gibberella*), blast (genus *Pyricularia*), leaf spot (genus *Cochliobolus*), damping-off (genus *Fusarium*), damping-off (genus *Pythium*), damping-off (genus *Rhizopus*), damping-off (genus *Trichoderma*).

Suitable examples of the plant diseases on which the composition of the present invention has a controlling effect include diseases caused by genus *Fusarium*. In particular, the composition of the present invention exhibit an excellent controlling effect on the diseases caused by genus *Fusarium* such as celery yellows, lily rot, tomato wilt, and aster wilt.

The plant disease controlling method of the present invention (hereinafter also referred to as "the controlling method of the present invention") comprises generally applying an effective amount of the composition of the present invention to a plant or an area in which a plant is grown.

When the composition of the present invention is to be applied to a plant, it may be applied to stems and leaves of plants, seeds of plants, roots of plants or bulbs of plants. The bulbs as used herein include scaly bulbs, corms, root stalks, tubers, tuberous roots, and rhizophores.

Specific examples of the controlling method of the present invention include treatment of stems and leaves of plants, soil treatment, treatment of seeds of plants such as seed disinfection and seed coating, treatment of roots of plants, and treatment of bulbs (e.g., seed tubers) of plants. These controlling methods may be used in combination.

Examples of the treatment of stems and leaves of plants include application to the surface of plants such as foliage application and stem application.

Examples of the soil treatment method include spraying over the soil, soil incorporation, soil irrigation with a chemical solution, soil injection of a chemical solution, chemical solution drip, and immersion of soil in a chemical solution. Examples of a subject of the soil treatment may include a planting hole, a planting row, the vicinity of a planting hole, the vicinity of a planting row, the entire surface of a cultivation area, a plant foot, spaces between plants, area beneath the trunk, main furrow, ridge soil, a nursery box, a nursery tray, or a nursery bed. The soil treatment may be conducted before sowing, at the time of sowing, immediately after sowing, in a raising seedling stage, before transplanting, at the time of transplanting, or in a growing stage after transplanting. In the soil treatment, the active ingredient may be mixed with an irrigation liquid, and examples thereof include injecting to irrigation facilities such as irrigation tube, irrigation pipe and sprinkler, mixing into flooding liquid between planting rows and mixing into culture solution.

Examples of the treatment of seeds, roots or bulbs in the controlling method of the present invention include a spraying treatment in which a suspension of the composition of the present invention is atomized and sprayed over surfaces of seeds or bulbs, an smearing treatment in which a wettable powder, an emulsifiable concentrate or a suspension concentrate of the composition of the present invention is applied to seeds or bulbs with a small amount of water added or without dilution, an immersion treatment in which seeds, roots or bulbs are immersed in a solution of the composition of the present invention for a certain period of time, a film coating treatment, and a pellet coating treatment.

The amount of the composition of the present invention in each application may be typically $10^3$ to $10^{15}$ CFU, preferably $10^3$ to $10^{12}$ CFU, more preferably $10^5$ to $10^{10}$ CFU per 1 plant. The emulsifiable concentrates, wettable powders, suspension concentrates or the like are typically diluted with water, and then applied. The granules or the like are typically applied without being diluted.

The controlling method of the present invention is used in agricultural lands such as fields, paddies, lawns, orchards or non-agricultural lands.

The composition or method of the present invention can be used to control diseases in agricultural land where "plants" as listed below are grown without causing damage by chemicals to the plants.

Crops: corn, rice, wheat, barley, rye, oat, sorghum, cotton, soybean, peanut, buckwheat, sugar beet, rapeseed, sunflower, sugar cane, tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, squash, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, etc.;

Flowers;

Foliage plants;

Lawns;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, Chinese date, coconut, etc.;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, etc.), etc.

The "plants" as mentioned above also include those to which tolerance to HPPD inhibitors such as isoxaflutole, ALS inhibitors such as imazethapyr and thifensulfuron-methyl, EPSP synthetase inhibitors, glutamine synthetase inhibitors, and herbicides such as bromoxynil and dicamba has been conferred by a classical breeding method or genetic engineering.

The plants include those genetically engineered to be able to synthesize selective toxins (for example, insecticidal proteins derived from *Bacillus cereus, Bacillus popilliae, Bacillus thuringiensis*, etc.) as known in genus *Bacillus*.

The toxins contained in such genetically engineered plants are able to confer resistance particularly to *Coleoptera, Diptera* and *Lepidoptera* to the plants.

The "plants" include those produced by using a genetic engineering technique, which have ability to generate antipathogenic substances (e.g., a PR protein, ion channel inhibitors) having selective action.

The above-mentioned "plants" also include those having a plurality of the above characters such as herbicide tolerance, harmful insect resistance and disease tolerance, which have been conferred by a classical breeding method or genetic engineering, and those having a plurality of the above characters, which have been conferred by hybridizing a plurality of genetically engineered parent plants having the same or different characters.

Among the diseases occurred in these plants, the diseases caused by genus *Fusarium* such as celery yellows, lily rot, tomato wilt and aster wilt are expected to be particularly controlled by the composition of the present invention.

The present invention will be described in more detail by way of the following Examples, but the present invention is not limited only to them.

Example 1

Separation and Selection of Microorganisms Belonging to Genus *Plectosphaerella* and Having Controlling Activity on Celery Yellows A section was produced from a vascular tissue of root in a healthy celery showing no disease symptoms in an agricultural field where celery yellows occurs at a high level. The section was placed on the flat surface of a plain agar medium containing 50 ppm of chloramphenicol, and then the medium was put into an incubator at 25° C. and allowed to stand for culturing microorganisms present in the section.

The hyphal tips of microorganisms extending from the section were transplanted onto the flat surface of a plain agar medium. After that, microorganisms grown on the plain agar medium were transplanted onto the flat surface of a potato extract agar medium containing glucose and then cultured. From the filamentous fungi obtained after the culturing on a potato extract agar medium containing glucose, strains having a conidium formed on a condiophore were collected.

The collected strains were cultured on a PDA flat medium at 25° C. for 14 days. Then, 24 microorganisms having the following features were separated from the cultured microorganisms.

Colony; pale orange—cream colored, moist, having a flat surface.

Condiophore; unbranched or branched, rising perpendicularly from vegetative hypha.

Conidium; mainly cylindrical two-cell type, when observed from the site at the tip of phialide (conidium-forming cells), formed in the conidium mass.

Each of the separated microorganisms was cultured in a PDB medium at 25° C. for 7 days, and then diluted with demineralized water to prepare a microorganism suspension at the concentration of $2 \times 10^7$ CFU/ml.

Celery seedlings (cultivar: Cornell 619) at 2.5 leaf stage were subjected to irrigation treatment with each suspension at the rate of 10 ml per one seedling. Two days after the irrigation treatment, the celery seedlings were transplanted into a pot with a diameter of 10.5 cm, and immediately subjected to irrigation treatment with a suspension of the pathogenic microorganism of celery yellows (*Fusarium* oxysporum f.sp. apii) at the rate of 10 ml per one seedling. Said suspension of the pathogenic microorganism of celery yellows was prepared by diluting the culture of the pathogenic microorganism of celery yellows cultured in a bran-vermiculite medium at 25° C., with demineralized water to be a concentration of $2 \times 10^6$ CFU/ml.

The above celery seedlings treated with the pathogenic microorganism of celery yellows were cultivated in a Biotron at 25° C., 20000 lux. Thirty days after the pathogen inoculation, the disease severity of celery yellows was determined.

The disease severity and the controlling value were calculated by using the following formulae, and 2 strains having a controlling activity on celery yellows (not less than 40 of the controlling value) were selected.

Disease severity=Σ(disease index of each seedling× number of each seedling)×100/(3×number of tested seedling)

Controlling value=100×(1−disease severity in treated section/disease severity in non-treated section)

Disease index 0: no onset of disease, 1: slight browning in the root vascular bundle, 2: severe browning in the root vascular bundle, 3: very severe browning and partial rot in the root vascular bundle.

The BLAST homology search of the selected 2 strains was conducted for 28S-rDNA-D1/D2 base sequence by using international base sequence databases such as GenBank/DDBJ/EMBL and confirmed that the selected 2 strains have a homology of 98.7% to 28S-rDNA-D1/D2 base sequence from *Plectosphaerella cucumerina* (accession No. U17399), thereby separating and selecting 2 strains (*Plectosphaerella* sp. strain KFC005, *Plectosphaerella* sp. strain KFC015) that belongs to genus *Plectosphaerella* and a controlling activity on celery yellows. The 28S-rDNA-D1/D2 base sequences of the strains KFC005 and KFC015 are shown in Sequence No. 1 and Sequence No. 2, respectively.

These strains were deposited at International Patent Organism Depositary, National Institute of Advanced Industrial Science and Technology (Tsukuba Central 6, 1-1-1 Higashi, Tsukuba, Ibaraki 305-8566 Japan) on Nov. 10, 2008 with accession Nos. FERM BP-11196 and FERM BP-11197, respectively, and have been stored at the institute.

The obtained disease severity and controlling value are shown in Table 1.

TABLE 1

Controlling effect on celery yellows

| Strain | Disease severity | Controlling value |
|---|---|---|
| KFC005 | 41.7 | 52.3 |
| KFC015 | 50.0 | 42.9 |
| Non-treated section | 87.5 | 0 |
| Pathogen-free section | 0.0 | — |

Example 2

Controlling Effect on Lily Rot

The filamentous fungus genus *Plectosphaerella* KFC005 was cultured in a PDB medium, filtrated with a two-ply gauze, and diluted with demineralized water to prepare a suspension of KFC005 at a concentration of $9 \times 10^6$ CFU/ml.

Lily seedlings (cultivar: Lilium×formolongo) at 2-3 true leaf stage were subjected to irrigation treatment with the above suspension of KFC005 at the rate of 10 ml per one seedling. Two days after the irrigation treatment, the lily seedlings treated with KFC005 were transplanted into a Poly-Pot with a diameter of 9 cm, which was charged with a soil where lily rot was occurring. Thirty days after the transplantation, the disease severity was determined. The disease severity and the controlling value were calculated by using the following formulae. The disease severity and the controlling value are shown in Table 2.

Disease severity=τ(disease index of each seedling× number of each seedling)×100/(3×number of tested seedling)

Controlling value=100×(1−disease severity in treated section/disease severity in non-treated section)

Disease index 0: no onset of disease, 1: yellowing in a part of leaves, wilting, 2: yellowing in a number of leaves, wilting, and poor growth, 3: very poor growth or death

TABLE 2

Controlling effect on lily rot

| Strain | Disease severity | Controlling value |
|---|---|---|
| KFC005 | 6.7 | 90.9 |
| Non-treated section | 73.3 | 0 |

Example 3

Controlling Effect on Tomato Wilt

The filamentous fungus genus *Plectosphaerella* KFC005 and the filamentous fungus genus *Plectosphaerella* KFC015 were cultured in a PDB medium, filtrated with a two-ply gauze, and diluted with demineralized water to prepare a suspension at a concentration of $2 \times 10^5$ CFU/ml and $5 \times 10^4$ CFU/ml $9 \times 10^6$ CFU/ml, respectively. Tomato seedlings (cultivar: Patio) at 5 leaf stage, one week before settled planting, were subjected to irrigation treatment with each suspension at the rate of 15 ml per one seedling, and the same treatment was repeated 3 days before settled planting.

The treated tomato seedlings were transplanted into a plastic tray with a volume of about 500 cm³ (4 seedlings/tray), and immediately after that, they were subjected to irrigation treatment with a suspension of the pathogenic microorganism of tomato wilt at 25 ml per one seedling. Said suspension of the pathogenic microorganism of tomato wilt was prepared by diluting the culture of the pathogenic microorganism of tomato wilt (*Fusarium oxysporum* f.sp. *lycopersici*) cultured in a PDB medium at 30° C. for 7 days, 10 times with demineralized water.

Sixty days after the pathogen inoculation, the seedlings were examined, and the disease severity and the controlling value were calculated by using the following formulae. The obtained disease severity and controlling value are shown in Table 3.

Disease severity=(disease index of each seedling× number of each seedling)×100/(433 number of tested seedling)

Controlling value=100×(1−disease severity in treated section/disease severity in non-treated section)

Disease index 0: no onset of disease, 1: browning in less than ¼ of the root vascular bundle, 2: browning in not less than ¼ and less than 2/4 of the root vascular bundle, 3: browning in not less than 2/4 and less than ¾ of the root vascular bundle, 4: browning in not less than ¾ of the root vascular bundle.

TABLE 3

Controlling effect on tomato wilt

| Strain | Disease severity | Controlling value |
|---|---|---|
| KFC005 | 15.9 | 55.1 |
| KFC015 | 18.8 | 46.9 |
| Non-treated section | 35.4 | 0 |
| Pathogen-free section | 0.0 | — |

Example 4

Controlling Effect on Aster Wilt

The filamentous fungus genus *plcrtnephaerella* KFC005 was cultured in a PDB medium, filtrated with a two-ply gauze, and diluted with demineralized water to prepare a suspension of KFC005 at a concentration of $9 \times 10^6$ CFU/ml.

Aster seedlings (cultivar: Hanawhite, small flower aster, seedlings grown in 288 pole cell) were transplanted into a pot No. 2.5 charged with a soil where aster wilt was occurring at a high level.

The aster seedlings were subjected to irrigation treatment with the above suspension at the rate of 10 ml per one seedling. Forty days after the pathogen inoculation, the seedlings were examined, and the disease severity and the controlling value were calculated by using the following formulae. The obtained disease severity and controlling value are shown in Table 4.

Disease severity=(disease index of each seedling×
number of each seedling)×100/(4×number of
tested seedling)

Controlling value=100×(1−disease severity in treated
section/disease severity in non-treated section)

Disease index 0: no onset of disease, 1: onset of disease in less than ¼ of stem, 2: onset of disease in about ½ of stem, 3: onset of disease in about ¾ of stem, 4: death.

TABLE 4

Controlling effect on aster wilt

| Strain | Disease incidence | Disease severity | Controlling value |
|---|---|---|---|
| KFC005 | 57.1 | 32.1 | 48.6 |
| Non-treated section | 70.0 | 62.5 | 0 |

Example 5

Production of the Composition of the Present Invention

The filamentous fungus genus *Plectosphaerella* KFC005 is cultured in a PDB medium and filtrated with a two-ply gauze. The resultant suspension of microorganism is centrifuged at 6000 rpm for 10 minutes to remove the supernatant. Then, 10% aqueous suspension of bentonite is added to the precipitated micoroorganisim in tenfold amount of the wet weight of the microorganism. The resultant mixture is lyophilized to obtain a plant disease controlling composition containing filamentous fungus genus *Plectosphaerella* KFC005 as an active ingredient.

Example 6

Culture Method for the Microorganism of the Present Invention

The filamentous fungus genus *Plectosphaerella* KFC015 is cultured in a PDB medium, and diluted 10 times with sterilized water. The dilution (100 ml) is mixed well with a sterilized bran (100 g), and further cultured at 25° C. for 2 weeks.

INDUSTRIAL APPLICABILITY

According to the invention, a plant disease controlling composition and a plant disease controlling method, which are useful for the cultivation of specially cultivated agricultural products or organic agricultural products, can be provided.

The invention claimed is:

1. A plant disease controlling composition comprising as an active ingredient a microorganism belonging to genus *Plectosphaerella* and having a plant disease controlling ability,
wherein the microorganism is *Plectosphaerella* sp, strain KFC005 (FERM BP-11196), or *Plectosphaerella* sp, strain KFC015 (FERM BP-11197).

2. The plant disease controlling composition according to claim 1, wherein the plant disease is a disease caused by genus *Fusarium*.

3. The plant disease controlling composition according to claim 2, wherein the disease caused by genus *Fusarium* is celery yellows, lily rot, tomato wilt, or aster wilt.

4. A method for controlling a plant disease, which comprises applying an effective amount of the plant disease controlling composition according to claim 1.

5. *Plectosphaerella* sp, strain KFC005 (FERN BP-11196).

6. *Plectosphaerella* sp, strain KFC015 (FERM BP-11197).

* * * * *

SEQUENCE LISTING

```
<160> NUMBER OF SEQ ID NOS: 2

<210> SEQ ID NO 1
<211> LENGTH: 612
<212> TYPE: DNA
<213> ORGANISM: Plectosphaerella sp.

<400> SEQUENCE: 1
gcatatcaat aagcggagga aaagaaacca acagggattg cctcagtaac ggcgagtgaa      60
gcggcaacag ctcaaatttg aaatctggct ccttcggggt ccgagttgta atttgcagag     120
gatgcgtcgg gtacgggtcc ctaccgagtt ccctggaacg ggacgccata gagggtgaga     180
gccccgtctg gtaggatacc cagcccatgt gacgctccct cgacgagtcg agtagtttgg     240
gaatgctgct ctaacgggag gtatactcct tccaaagcta aataccggct ggagaccgat     300
agcgcacaag tagagtgatc gaaagatgaa aagcactttg aaaagagagt caaacagcac     360
gtgaaattgt taaaagggaa gcactcgcta ccagacttgg gtttggcggt tcaaccgggg     420
ccacgccccg gggcattccg ccagctcagg ccagcatcag ctttccgtcg ggggcaaaga     480
cgtcgggaat gtggctcccc ctcggggag tgttatagcc cggcgtgtca taccttcgg      540 ggggctgagg tacgcgcttc tgcaaggatg ctggcgtaat ggtagctagt gacccgtctt     600
gaaacacgga cc                                                        612

<210> SEQ ID NO 2
<211> LENGTH: 612
<212> TYPE: DNA
<213> ORGANISM: Plectosphaerella sp.

<400> SEQUENCE: 2
gcatatcaat aagcggagga aaagaaacca acagggattg cctcagtaac ggcgagtgaa      60
gcggcaacag ctcaaatttg aaatctggct ccttcggggt ccgagttgta atttgcagag     120
gatgcgtcgg gtacgggtcc ctaccgagtt ccctggaacg ggacgccata gagggtgaga     180
```

```
gccccgtctg gtaggatacc cagcccatgt gacgctccct cgacgagtcg agtagtttgg        240
gaatgctgct ctaacgggag gtatactcct tccaaagcta aataccggct ggagaccgat        300
agcgcacaag tagagtgatc gaaagatgaa aagcactttg aaaagagagt caaacagcac        360
gtgaaattgt taaaagggaa gcactcgcta ccagacttgg gtttggcggt tcaaccgggg        420
ccacgccccg gggcattccg ccagctcagg ccagcatcag ctttccgtcg ggggcaaaga        480
cgtcgggaat gtggctcccc ctcggggag tgttatagcc cggcgtgtca tacccttcgg         540
ggggctgagg tacgcgcttc tgcaaggatg ctggcgtaat ggtagctagt gacccgtctt        600
gaaacacgga cc                                                            612
```